(12) United States Patent
Ericson et al.

(10) Patent No.: US 6,733,471 B1
(45) Date of Patent: May 11, 2004

(54) HEMOSTATIC SYSTEM AND COMPONENTS FOR EXTRACORPOREAL CIRCUIT

(75) Inventors: Daniel G. Ericson, Rochester, MN (US); Eric J. Thor, Arden Hills, MN (US); William S. Haworth, Scotland (GB)

(73) Assignee: Medtronic, Inc., Minneapolis, MN (US)

( * ) Notice: Subject to any disclaimer, the term of this patent is extended or adjusted under 35 U.S.C. 154(b) by 403 days.

(21) Appl. No.: 09/662,044

(22) Filed: Sep. 15, 2000

Related U.S. Application Data

(63) Continuation of application No. PCT/US99/05679, filed on Mar. 15, 1999.
(60) Provisional application No. 60/078,054, filed on Mar. 16, 1998.

(51) Int. Cl.$^7$ .......................... A61M 37/00; A61M 1/36; B01D 11/00; C02F 1/00
(52) U.S. Cl. .................... 604/4.01; 604/5.01; 604/6.09; 422/44; 128/DIG. 3; 210/645; 210/739; 210/743; 210/198.1; 210/348
(58) Field of Search ................ 604/4.01, 6.01, 604/5.01–5.04, 6.09, 6.16, 19, 27, 28, 65–67, 500, 503, 504; 128/DIG. 3, 898; 422/44–48; 210/645–47, 650–51, 739, 743, 767, 746, 85, 96.1–96.2, 198.1, 321.6, 348, 418, 929; 600/300–1, 309, 310, 314, 316, 322–24, 326, 334, 347–48, 352, 361, 366–69, 437–39, 459, 466–68, 504–5

(56) References Cited

U.S. PATENT DOCUMENTS

| | | |
|---|---|---|
| 3,848,580 A | 11/1974 | Hyden et al. .................. 128/2 |
| 4,401,431 A | 8/1983 | Arp ................................. 604/4 |
| 5,308,320 A | 5/1994 | Safar et al. ..................... 604/4 |
| 5,725,492 A | 3/1998 | Igo et al. ........................ 604/4 |

FOREIGN PATENT DOCUMENTS

| | | |
|---|---|---|
| WO | WO 96/35954 | 5/1996 |
| WO | WO 97/32653 | 3/1997 |

OTHER PUBLICATIONS

Cosgrove, et al., ("Aprotinin Therapy for Reoperative Myocardial Revascularization: A Placebo–Controlled Study", *Ann. Thorac. Surg.* 54:1031–1038, 1992).

Levy et al. ("A Multicenter, Double–Blind, Placebo–Controlled Trial of Aprotinin for Reducing Blood Loss and the Requirement for Donor–Blood Transfusion in Patients Undergoing Repeat Coronary Artery Bypass Grafting", *Anesth. Analg.* 81:35–37, 1995).

E. Bennett–Gurrero, et al., ("ε–Aminocaproic Acid Administration and Stroke Following Coronary Artery Bypass Graft Surgery", *Ann. Thorac. Surg.* 67:1283–1287, 1999).

*Primary Examiner*—Patricia Bianco
(74) *Attorney, Agent, or Firm*—Fredrikson & Byron P.A.

(57) ABSTRACT

A method and system for use in the course of extracorporeal blood flow, e.g., cardiopulmonary bypass, dialysis, and angioplasty procedures, in order to reduce or minimize inflammation, excessive bleeding, and other undesirable side effects. The system can include one or more automated blood parameter sensor modules and one or more blood parameter regulating modules. The system is particularly well suited to monitor and/or regulate blood parameters that include blood analytes (e.g., biomolecules, drugs or metabolites) as well as blood functions (e.g., clotting time, fibrinolytic activity, immune response). The system is particularly well suited for use in the management of clotting (e.g., heparing/protamine) and bleeding (e.g., aprotinin).

58 Claims, 4 Drawing Sheets

HEMOSTATIC SYSTEM AND COMPONENTS FOR EXTRACORPOREAL CIRCUIT

CROSS REFERENCE TO RELATED APPLICATIONS

The present application is a continuation of and claims priority to International Application No. PCT/US99/05679 (published as International Publication No. WO 99/47190), filed Mar. 15, 1999 and designating the United States, which in turn claims priority from Provisional Application No. 60/078,054, filed Mar. 16, 1998, the entire disclosure of which is incorporated herein by reference.

TECHNICAL FIELD

The present invention relates to surgical and other procedures, such as cardiopulmonary bypass procedures, that involve the use of extracorporeal blood flow. In a related aspect the invention relates to sensors and filters for determining and affecting the presence or level of blood components such as heparin and administered drugs and their metabolites.

BACKGROUND OF THE INVENTION

The heart-lung machine is a system used for cardiopulmonary bypass ("CPB"). Since the development of a prototype system by Dr. John Gibbon in 1953, the use of CPB has evolved to the point where it is now commonplace, and permits major surgical procedures to be performed on the heart.

While on bypass, the blood flow is diverted around the heart and lungs, as a machine takes over the responsibility of both oxygenating the blood and maintaining blood flow. Cardiopulmonary bypass permits the surgeon to operate on the heart while the heart-lung machine sustains circulation throughout the body. Oxygen-poor blood that would normally enter the heart through the superior and inferior vena cavae, is shunted off through the superior vena caval cannula and the inferior vena caval cannula. Once oxygenated, the blood is returned to the body through the aortic cannula.

The typical CPB circuit includes several components, including one or more oxygenators, heat exchangers, tubing sets, filters, pumps and reservoirs. The circuit is often used, in turn, in combination with one or more drugs such as heparin, which is an anticoagulant that is both administered intravenously and can be used to coat blood contacting surfaces. At the conclusion of surgery, the presence and effect of heparin is reversed, typically in a rapid manner, by the administration of a drug such as protamine. Protamine, which is derived from salmon sperm, is highly positively charged and serves to effectively neutralize the negatively charged heparin in a cationic/anionic interaction. Protamine, however, has its own drawbacks, in the form of potential allergenic and inflammatory responses.

Extracorporeal circulation, such as that used during cardiopulmonary bypass, continues to be associated with various drawbacks, however, including both inflammation and excessive bleeding. The inflammatory response is believed to be caused, or exacerbated, by various factors, including the various flow forces (e.g., shear associated with turbulence and suction) involved in CPB, and by the exposure of blood to both foreign surfaces and to air. Exposure of the blood to oxygenators, pumps, and blood salvage and tubing sets, is well documented to activate inflammation responses during and post bypass procedures. In addition, the process of removing the anticoagulant heparin, post bypass, by addition of protamine is also documented to activate inflammatory processes. Inflammation, in turn, can cause both cell damage and diminished organ function, leading to increased morbidity and a longer recovery time with an increase in both length of hospital stay and costs.

Inflammatory injury occurs when the patient's own blood, after circulating through the CPB circuit is returned to the patient. The inflammation reaction induced by extracorporeal circulation also has the potential of increasing patient risk of inducing the "whole body inflammatory response" and ensuing organ failure. Approximately 600,000 cardiac surgical procedures requiring CPB are performed annually in North America and approximately 400,000 in the rest of the world. Most, if not all, of such procedures involve the need to monitor both heparin concentration and whole blood Activated Clotting Time (ACT).

As mentioned above, the use of heparin and protamine may be associated with a number of adverse effects. Close monitoring of the heparin concentration and clotting time is required due to risk of clotting, if the heparin levels drop excessively low. Similarly, excessively high levels of heparin can require correspondingly high dosages of protamine. Although life-threatening, protamine-related reactions occur in less than 5% of cardiac surgical patients. Still, the use of protamine is broadly problematic and severe reactions to protamine complex are idiosyncratic.

Moreover, protamine is difficult to titrate. The existence of many dosing regimes attests to the fact there is no agreement among practitioners as to how best the drug should be used. Protamine may be dosed on the basis of 1) body weight or surface area, 2) by a fixed ratio to the initial dose of heparin, 3) by fixed ratio according to the total heparin dose, or 4) by response to the activated clotting time (ACT). Because protamine itself has anticoagulant properties when given in excess, the ideal protamine dose results in plasma levels just exceeding the heparin concentration. However, there is evidence that fixed-ratio dosing schemes tend to result in excessive protamine administration.

While the ACT is used as a functional test for the adequacy of heparin reversal, it does not provide an index of how much protamine is required to reverse heparin. This is, in part a function of large patient-to-patient variability in heparin pharmacodynamics and pharmacokinetics (e.g., the half-life for heparin may vary for 30 min to 2 hr). While this functional test is used in practice when bleeding is present, additional repeated doses of protamine are often given even when the ACT is normal.

These and other complications associated with heparin and protamine dictate that management of patient's heparin concentration and clotting time be closely monitored. Typically, however, heparin concentration is not accurately recorded during CPB, due largely to the lack of suitable methods and instrumentation. At most, some facilities measure a heparin concentration "range" by removing plasma and performing a heparin determination by protamine titration, using a commercially available device. Such an approach has several drawbacks, however, including the lack of a direct measurement of heparin concentration, the need for manual blood draws, and heparin concentrations that are provided in gross increments.

Another complication of surgical procedures that involve CPG is excessive bleeding. A recently approved drug known as aprotinin can effectively reduce blood loss and decrease the need for transfusions. Aprotinin was studied for use mainly in heart surgery because the circulation of the blood outside the body in this surgery increases the likelihood of excessive bleeding during and after surgery.

Aprotinin (TRAYSL™, Bayer) is a natural protease inhibitor derived from bovine lung, and acts by inhibiting trypsin, chymotrypsin, plasmin, tissue plasminogen activator, and kallikrein, thereby directly affecting fibrinolysis. It also inhibits the contact phase activation of coagulation which initiates coagulation and promotes fibrinolysis. In addition, aprotinin preserves the adhesive glycoproteins in the platelet membrane, rendering them resistant to damage from the increased plasmin levels and mechanical injury that occur during cardiopulmonary bypass. The net effect is to inhibit both fibrinolysis and turnover of coagulation factors and to decrease bleeding. T1/2, IV: 150 min with a terminal elimination phase half-life of 10 hr. Aprotinin is slowly broken down by lysosomal enzymes, although depending on the dose, up to 9% may be excreted through the urine unchanged.

Although aprotinin was studied in the 1960's, low doses were evaluated in an effort to treat bleeding after cardiac surgery rather than to prevent it. However, it was not until the late 1980's that prothylactic use was reported. Royston developed a pharmacologic approach to inhibit inflammatory responses during CPB administering that includes a loading dose of 2 million units of aprotinin following intubation, and a continuous infusion of 500,000 units/hour with a CPB pump prime dose of 2 million units. This has become known as the high dose or "Hammersmith regimen". In patient's receiving aprotinin, chest tube drainage was 286 ml as compared to 1509 ml in the control.

In the United States approximately 20% of all CPB cases presently also incorporate the use of aprotinin, while in Europe about 80% of CPB cases presently use aprotinin. Postoperative bleeding is a cause of morbidity and mortality in this patient population. Extracorporeal circulation makes cardiac surgery possible but requires complete anticoagulation with heparin because the CPB apparatus and procedure is thrombogenic. During CPB, systemic anticoagulation is achieved with a loading dose of heparin (300–400 IU/kg) to achieve an Activated Clotting Time (ACT) of >500 seconds (normal non anticoagulated blood has an ACT time range of 80–110 seconds). This anticoagulation level of >500 seconds is targeted so as to preserve normal blood fluidity and limit blood clot formation to vascular injury sites. At the completion of the CPB case, the circulating heparin is reversed with protamine sulfate. While the ACT is used as a functional test for the adequacy of heparin reversal, it does not provide an index of how much protamine is required to reverse heparin. This is in part a function of large patient-to-patient variability in heparin pharmacodynamics and pharmacokinetics (the half-life for heparin may vary for 30 min to 2 hr). While this functional test is used in practice when bleeding is present, additional repeated doses of protamine are often given when the ACT is normal.

In redo CABG patients, Cosgrove, et al., (Ann. Thorac. Surg. 54:1031–1038, 1992) reported 171 patients who received either high dose aprotinin (Hammersmith dose), low dose aprotinin (half Hammersmith dose), or placebo. They found that low dose aprotinin was as effective as high dose aprotinin in decreasing blood loss and blood transfusion requirements. In contrast, Levy et al. (Anesth. Analg. 81:35–37, 1995) also reported the use of four different treatment groups in 287 patients undergoing repeat CABG surgery. Transfusion of allogenic packed RBC's was significantly less in the aprotinin treated patients compared to the placebo, with even greater reductions in total blood products exposure in high dose and half dose groups compared to placebo or pump prime cohorts.

The Full Hammersmith regimen of aprotinin reduces transfusion requirements and results in aprotinin concentrations reported to be in the range of 127–191 Kallikrein Inhibitory Units per millilter ("KIU/mL") at the end of one to two hours of CPB. This dosing regimen calls for an infusion of $0.5 \times 10^6$ KIU per hour from skin incision to completion of surgery in addition to $2 \times 10^6$ KIU added to the CPB pump prime solution. This dosing regimen attempts to maintain a plasma aprotinin concentration of 200 KIU/mL during CPB. Although concentrations of approximately 50 KIU/mL decrease fibrinolysis through inhibition of plasmin, a higher concentration (approx. 200 KIU/mL) appears to be necessary in order to inhibit kallikrein.

As recently reported by E. Bennett-Gurrero, et al., in the Annals of Thoracic Surgery, aprotinin concentrations in the range of 127–191 kallikrein inactivator units (KIU) at the end of CPB (<2hr duration) reduce transfusion requirements. It has been suggested that prolonged CPB may require higher infusion rates which significantly increase cost. Bennet-Guerrero reported that the cost for aprotinin given according to the Full Hammersmith regimen is $900–$1200 at Duke University Medical Center. The Duke group measured KIU and maintained these values between 127–191 KIU/mL.

There is no dispute that aprotinin reduces postoperative blood loss, however the dose regimen practices vary widely. Practice varies with the use of aprotinin in the prime, and use of either Full or Half Hammersmith. The parameters of successful levels of aprotinin protection are best measured in KIU. The dose of aprotinin obviously is related to the effect of the protease aprotinin on inhibition of kallikrein.

Since there is currently no way to provide a real time monitor for either aprotinin, per se, or its metabolic effectiveness, aprotinin tends to be provided in large doses and at multiple times during the CPB surgery, this in spite of its high cost. For instance, an initial test dose must be given 10 min prior to the loading dose. The test dose is followed by a loading dose, which is then followed by a constant infusion dose. In addition, a "pump prime" dose is added to the priming fluid of the cardiopulmonary bypass circuit by replacing an aliquot of the priming fluid prior to beginning cardiopulmonary bypass.

In spite of these and other advances, both inflammation and excessive bleeding continue to be common problems that plague the use of CPB. There clearly remains a need for new approaches to lessen or eliminate the inflammation that occurs in the course of CPB and other medical techniques that involve the extracorporeal circulation of blood.

SUMMARY OF THE INVENTION

Figure 1:
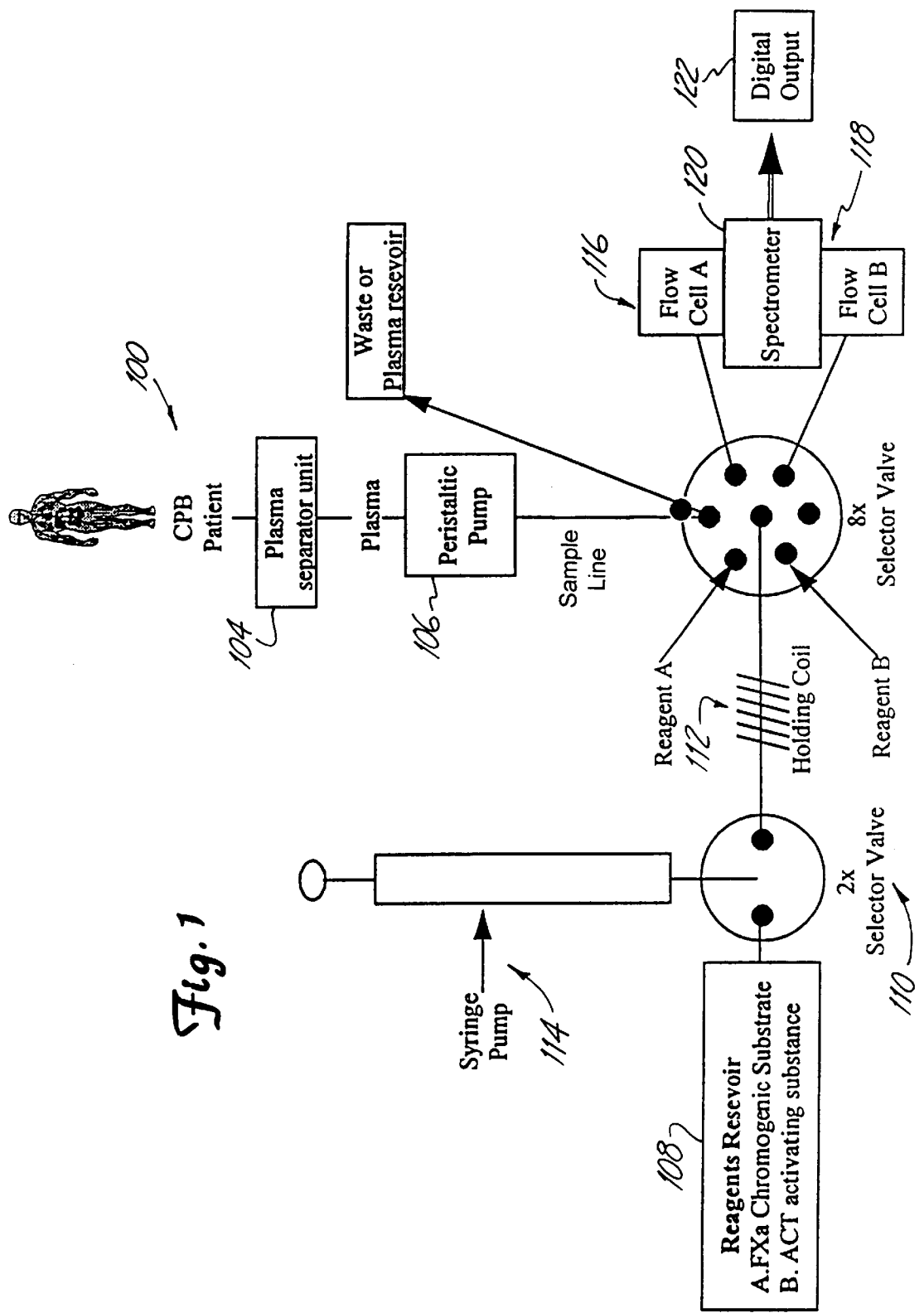
FIG. 1 shows a schematic view of sensor modules for both heparin and ACT for use in a system of the present invention.

In one aspect the present invention relates to a system and related method for use in the course of medical procedures that involve extracorporeal blood flow, e.g., cardiopulmonary bypass, dialysis, and angioplasty procedures. The system can be used to reduce or minimize inflammation, excessive bleeding, and other undesirable side effects, and particularly those side effects that are amenable to being monitored and/or regulated in the course of the surgery or treatment. The system is particularly well adapted to address the adverse reactions related to the use of heparin and protamine in the course of coagulation management methodologies, as well as the practical difficulties in using drugs such as aprotinin. In another aspect, and in certain preferred embodiments, sensor modules and regulating modules of this invention are considered novel in their own right, and moreover, can be used for their intended purpose and without the need for an entire system as described herein.

In a preferred embodiment, the system includes one or more automated blood parameter sensor modules and one or more blood parameter regulating modules. A "blood parameter", as used in this sense, will generally refer to a blood analyte (e.g., biomolecule, drug or metabolite) or a blood function (e.g., clotting time, fibrinolytic activity, immune response). In the case where a single sensor module and single regulating module are used, it is preferred but not required that the blood parameter monitored by the sensor module be the same as, or functionally related to, the blood parameter being regulated, as can be the case with heparin, for instance. In situations where the parameters are the same, or related, the activity of the regulating module can be directly related to the monitored parameter (as by removing or adding a monitored analyte) or indirectly related (as by removing or adding a factor that affects a monitored blood function). Moreover, any such relationship can be in a directly, or inversely directly, proportional fashion.

A sensor module of this invention is preferably adapted to incorporate flow injection analysis ("FIA") techniques, and as such, includes a variety of automated components, including for instance, i) a blood withdrawal component with in-line access (and optionally and preferably including a plasma separator), ii) an analytical component (e.g., including a reaction coil and detector), and iii) a readout component, as well as such other components as disposable blood-contacting components, valves, pumps and controls. The sensor can provide semicontinuous and/or continuous (e.g., uninterrupted) sampling of the blood, in order to provide near real-time digital output readings of the monitored parameter, the timing of the readout being limited largely by the inherent timing of the automated sample handling and analytical assay itself.

A sensor module of this invention is adapted to independently monitor, directly or indirectly, the presence of one or more blood parameters (e.g., blood functions such as clotting time assays (such as activated clotting time ("ACT") or prothrombin time ("PT")) and/or analytes such as biomolecules, drugs or metabolites present in the blood). In a preferred embodiment, for instance, one or more sensor modules are adapted to monitor one or more blood parameters identified in the plasma, and selected from the group consisting of clotting time, heparin concentration, and aprotinin concentration. As used herein, the term "sensor module" will generally refer to the ability to monitor a single blood parameter. A plurality of such sensor modules might be configured, however, into the form of a single unit, optionally even sharing several components or aspects, but providing the ability to independently monitor an equal number of blood parameters.

A regulating module, in turn, can function by directly or indirectly removing, adding, and/or altering the physicochemical makeup of the blood, e.g., by affecting the level of a blood analyte or function. As such, the module can be in any suitable form e.g., the form of a filter for use in removing blood components such as heparin and inflammation mediators. In a preferred embodiment, the regulating module is driven by the patient's own hemodynamic pressure (e.g., by a pressure drop of between about 40 mm and about 80 mm Hg).

One or more corresponding regulating modules, in turn, can be included in the system and adapted to affect the blood parameter(s) being monitored, e.g., by affecting the concentration and/or activity of one or more blood modules. In so doing, the filter permits the operator, or the system itself, to detectably and promptly alter the concentration, form and/or presence of the blood analyte.

In one embodiment, for instance, the detected blood parameter and filtered component are identical, such as in the preferred embodiment regarding heparin. In such an embodiment, heparin concentrations can be determined by the sensor and monitored in the course of removing heparin from the blood using a corresponding heparin filter module. In another embodiment, the monitored blood parameter is a blood function, such as clotting time, and a corresponding filter is used to affect a biomolecule or drug that directly or indirectly affects the function monitored by the sensor.

The use of a sensor, as described herein, can eliminate the need for the perfusionist or anesthesiologist to take time for "hands on" measurements. In turn, the system itself can be used to provide substantially "real-time" determinations of both blood parameter analyte (e.g., heparin) concentration and function (e.g., ACT times), therefore providing required patient data in a time frame not presently available in practice. A real-time heparin/clot management system, in turn, can improve patient outcome, for instance, by allowing tighter control of heparin and protamine dosing. The modules are adapted to be used separately or in any suitable combination, and can be independently incorporated either within or external to the blood flow path of a CPB circuit, as by appropriate access/sampling ports and shunting paths.

As an initial regulating module, a preferred system of this invention includes a blood flow-through device in the form of an inflammation filter, for use in removing inflammation mediators such as complement proteins and inflammatory cytokines from the blood. The inflammation filter can be incorporated at any juncture of an existing perfusion circuit (heart lung machine). A filter module of this type can be used, for instance, to remove anaphylatoxins such as C3a and C5a, chemokines such as interleukin(IL)-8 and RANTES, and proinflammatory cytokines such as IL-1, IL-6 and tumor necrosis factor alpha. Removal can be accomplished in any suitable manner, e.g., by the use of a support surface bearing a specific binding ligand, or by physicochemical means (e.g., adsorption to a hydrophobic surface). Suitable hydrophobic surfaces are selected, for instance, from the group consisting of acrylic polymers (e.g., acrylonitrile polymers, copolymers and polymer blends), polysulfones, polyamides (e.g., nylons such as Nylon-6, Nylon-6,6, Nylon-11, Nylon-12, Nylon 6,9, Nylon-12), and acrylic and methacrylic ester polymers (e.g., poly (methylmethacrylate)). These and similar materials have properties that lead to adsorption of inflammation activation components, especially the complement proteins C3a, C5a and Factor D.

In one embodiment, an inflammation filter for use as a regulating module of this invention is provided in the form of a flow through device that allows blood to come into contact with the surface area of a material surface that functions to remove the inflammation proteins. Such a module can include, for instance, a cartridge containing a hydrophobic support material and having both a blood inlet port and a blood out port at each end of the cartridge. The surface area, binding capacity and binding efficiency of the support material within the filter can be determined by those skilled in the art, in order to provide a desired rate and extent of removal, given the proteins and biological intermediates of interest and other considerations. Such a module can be designed to run at any flow rate that would be encountered during extracorporeal circulation.

A second preferred regulating (e.g., filter) module of this invention is used for the extracorporeal removal of heparin from the blood stream. In a preferred embodiment, for instance, the removal of heparin is accomplished by anionic exchange of heparin with an immobilized positively charged species on the surface of a membrane contained within the filter. For instance, the use of a suitable polyalkyleneimmine (e.g., polyethyleneimmine) as, or on, the surface of a suitable support (e.g., membrane or microfiber) provides an interactive surface that supports removal of heparin from circulation.

In a particularly preferred embodiment, a heparin filter is provided in the form of a flow through device that allows blood to come into contact with the surface area of a material having an affinity for the removal of heparin from the circulation of the patient. The surface area of the module can be determined as any surface area required to remove the circulating heparin concentration. The module can be run at any flow rate that would be encountered during extracorporeal circulation.

In a further preferred embodiment, the system of this invention includes a sensor module, e.g., in the form of a continuous and/or semi-continuous, and optionally, substantially "real time" sensor that can be used to measure the effect and/or kinetics of the use of one or more regulating modules as described herein. The sensor module(s) can be used at any or all times during the extracorporeal circulation procedure. For instance, a sensor module can be used to measure the kinetics of heparin removal by a heparin filter. In one embodiment, for instance, a heparin sensor employs the use of a plasma separation process that enables plasma to pass through a flow through cell for spectrophotometric determination of plasma heparin concentration. Heparin concentration is determined by mixing plasma with heparin sensitive dyes or substrates that include, but are not limited, to Azure A and chromogenic substrates for heparin and antithrombin. In a presently preferred embodiment, for instance, the sensor module includes a hollow fiber bundle, providing a low pressure gradient (supportable by the patient's own hemodynamics), capable of flow of about 1 liter/min to about 2 liters/min.

A heparin sensor module can be designed such that a small portion of blood passing through the tubing set of the perfusion circuit is shunted through the sensor configuration. Blood can separated to provide a plasma fraction in any suitable manner, e.g., by either the use of centrifugation or hemoconcentration across dialysis fibers. Plasma can then be mixed with exact volumes of heparin indicating dyes or chromogenic substrates. The treated plasma can then be measured by spectrophometric analysis and exact plasma heparin concentrations calculated and displayed.

The system, including modules and related method, of this invention provide new opportunities to the practitioner in the course of procedures involving extracorporeal blood flow, including the ability to periodically or continually monitor and/or regulate various blood parameters in order to better control such unwanted side effects as inflammation and excessive bleeding.

DETAILED DESCRIPTION

In one aspect, and in a particularly preferred embodiment, the described invention provides a system that can be used to reduce inflammation reactions by the use of one or more regulating modules, e.g., filters for the effective removal of inflammation activated proteins during extracorporeal circulation. In a similar aspect, the system can be used to both detect and remove heparin without activating, or exacerbating, the body's inflammation responses. Such a system can include at least three major modules, including a plurality of regulating modules such as blood component filters, and at least one sensor module. The system of this invention permits the operator to reduce the inflammation response induced by extracorporeal circulation. The various modules of the system can be provided and/or used individually or in combination to provide benefit to the patient.

A system of this invention can be used to improve the current methods of heparin management used today during cardiopulmonary bypass (CPB). In one such embodiment, the system includes a photometric based biosensor, which is used to provide a substantially real time coagulation management system that provides heparin concentration, clotting time, as well as aprotinin concentration measurement during CPB. Such a system can include the use of inexpensive disposable cartridges that can be inserted into a hardware device to measure the desired parameters. The system can also provide substantially real time heparin concentration with intermittent-automated clotting time. In addition, and also in a particularly preferred embodiment, the system further provides the ability to measure the levels and/or activities of other analytes, such as aprotinin. The aprotinin feature of such as system provides an inexpensive means of monitoring, controlling and dosing the expensive pharmacologic agent aprotinin.

Such a system can provide heparin, aprotinin and ACT measurements during CPB using instrumentation adapted to operating room practices and standards. Values obtained from the instrument are accurate and reliable, and can be used to provide standard curves for heparin concentration and aprotinin concentration that are comparable those obtained from existing technologies. The system provides a real time coagulation management system having the capability of providing benefit for the patient, the perfusionist, and the hospital itself.

A case for patient benefit of real time heparin and ACT monitoring was recently reported in Despotis, *Blood Coagulation and Fibrinolysis* (1997). This study was designed to determine prospectively if stable heparin concentration can be maintained during extracorporeal circulation by using a continuous infusion technique, compared with a bolus regimen based on whole blood heparin concentration monitoring. Despotis found that stable heparin concentrations were maintained using whole blood heparin measurements, whereas mean heparin concentrations were slightly lower using continuous infusion techniques. Despotis concluded that an optimal approach might involve the combined use of monitoring ACT and heparin concentration.

Aprotinin pharmacokinetics have, for the most part, been poorly understood, and in turn, the optimal dosing regimen for bypass cases has not been well defined. The Full-Hammersmith dosing regimen attempts to maintain a plasma aprotinin concentration of 200 KIU/ml during CPB. Although concentrations of approximately 50 KIU/ml decrease fibrinolysis through inhibition of plasmin, a higher concentration (approximately 200 KIU/ml) appears to be necessary in order to inhibit kallikrein. The 200 KU/ml concentration is based on in vitro studies and the aprotinin concentration necessary to achieve peak efficacy in vivo (during CPB) is not known. Accurate measurement of the KIU using the system of this invention can provide the ability to determine the optimal real time concentration, which in turn can reduce patient blood loss, and transfusion requirements.

A system of the present invention is also amenable to present day surgical instrumentation and methods, providing ease of use in the operating room. The present system can eliminate the need for the perfusionist or anesthesiologist to make multiple blood draws throughout the duration of the bypass procedure. The system can also conserve blood volume of the patient, and provide real time data output of heparin concentration, ACT and aprotinin concentration. Aprotinin typically costs between $1,000–1,500 per patient, and the dosing regimes used for this drug have no current monitor procedure. A system of this invention can be used to provide circulating aprotinin levels and/or information on aprotinin protease activity.

A system of this invention also provides a variety of advantages over current heparin management systems, which typically require repeated patient blood sample draws from an in-line arterial access. Typically a single bypass procedure requires between 8 and 15 such blood draws which require 3–5 ml of blood at each measurement. As a heparin/clotting management tool, the system of the present invention can instead be configured in the form of a dual plasma monitoring system that employs a spectrophotometric system that provides substantially realtime digital output of heparin concentration and activated clotting time (ACT) and aprotinin activity. Moreover, the disposable portions of the system, including its filter and sensor modules, can be adapted to be less expensive then the current costs of commercially available disposables for measuring heparin and ACT.

In a particularly preferred embodiment, the system is provided in the form of a fiber-optic system that combines and integrates existing biochemical approaches to heparin management with new and improved instrumentation and methodologies in order to permit measurements that will become standard in cardiac operating rooms. In such an embodiment, the system can include a state of the art Flow Injection Analysis (FIA) system, preferably in combination with a compact and portable automated Sequential Injection Analysis (SIA) system, in the manner described herein. Such a configuration can include, for instance, a multi-position selector valve, a multi-port microsyringe pump, and a multi-channel auxiliary peristaltic pump for waste and rinse lines. Moreover, the entire flow injection system can be controlled by a suitable computer and software package.

A regulating module for use in the present system, in the form of an inflammation filter, can be provided in any suitable form, e.g., in the form of a hydrophobic surface positioned with a flow chamber having blood inlet and blood outlet ports. The inflammation filter, in turn, can be positioned and incorporated at any suitable point and in any suitable fashion with the circuit. In one embodiment, for instance, only suctioned blood (e.g., from the pericardial cavity wound site and/or the ventricular cannula) is passed through the first filter, on the theory that suctioned blood is likely to have higher, and potentially problematic, levels of complement as compared to non-suctioned blood. In another embodiment, the complement filter can be used to remove one or more enzymes that convert complement from its inactive to active forms. In yet another embodiment the complement filter can be used as a continuous in line filter for activated complement.

A heparin filter, for use as a regulating module of this invention, can take any suitable form. Suitable heparin filters are available, for instance, from Akzo in the form of an affinity membrane device for whole blood (see, e.g., 15$^{th}$ Annual Meeting, International Society of Blood Purification, Sep. 11–13, 1997). Such filters, however, are typically less preferred for use in a system of this invention, in view of the fact that they employ a blood pump to provide a high pressure drop, and have a relatively low blood volume capacity.

Figure 3:
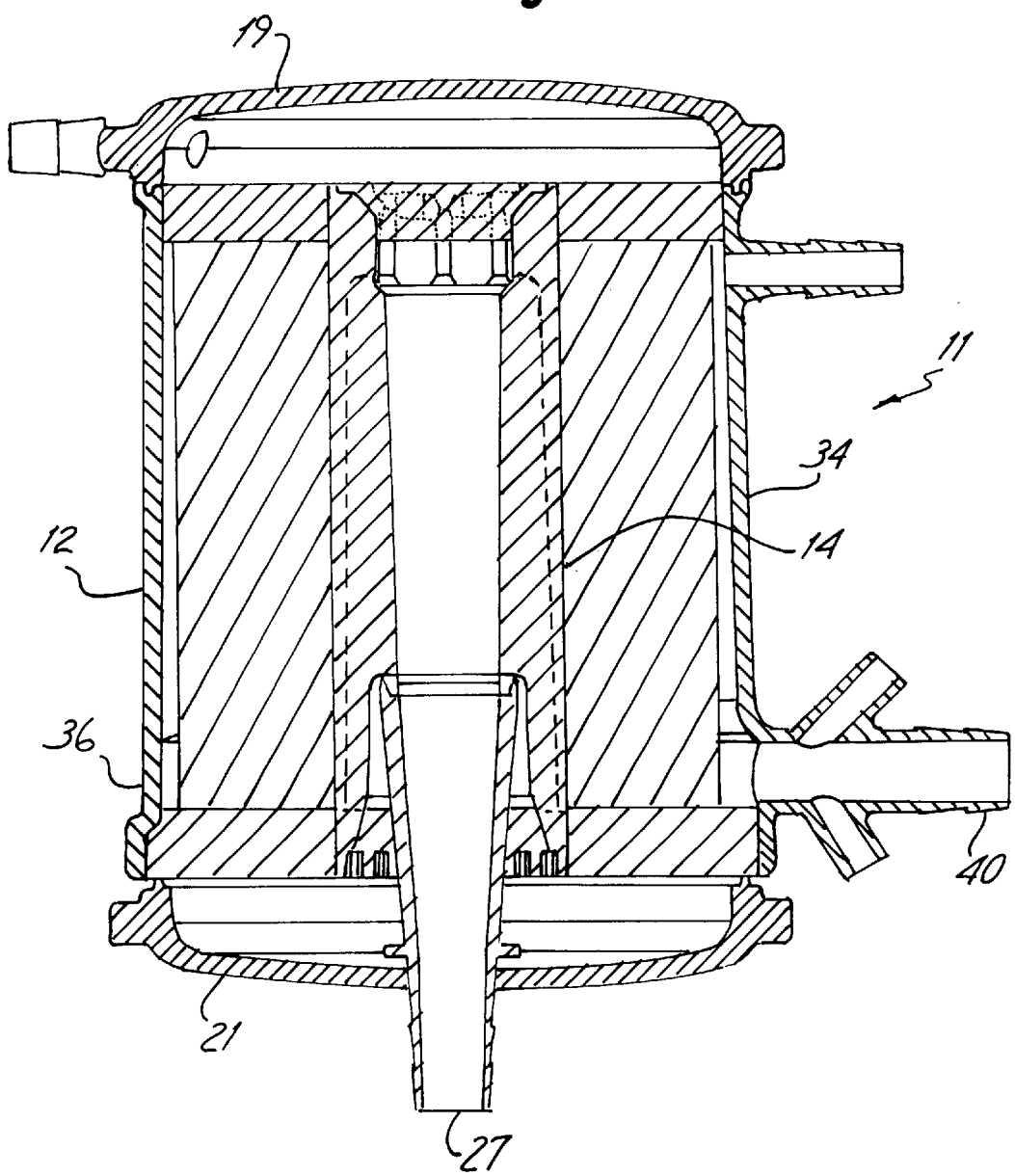
FIG. 3 shows an oxygenator device modified to perform as a heparin filter module of this invention.

A preferred heparin filter for use in the present invention can be made, for instance, by modifying conventional hollow fiber oxygenators. For example, a suitable heparin filter can be made by modifying a mass transfer device having a microporous hollow fiber bundle, as described in U.S. Pat. No. 5,376,334, the disclosure of which is incorporated herein by reference. A device as described in the '334 patent can be readily modified, e.g., by omitting or removing both the heat exchanger portion and the oxygenating inlet and cap, and replacing these portions with caps in order to employ only the extraluminal flow path and surfaces (see, for instance, FIG. 3 of the '334 patent). Present FIG. 3 shows a mass transfer device in the form of a heparin filter including a hollow fiber bundle wound on a supporting core for radially outward flow of a first fluid, such as blood. The top and bottom ends of the bundle are embedded in a solidified potting composition at the top and bottom ends of the unit. The core has an axis extending from one end to the other, and the hollow fiber bundle has packing fractions which increase radially outward of the core's axis for a major portion of the bundle.

The resulting module will be described by reference to present FIG. 3, using reference numbers identical to those of the '334 patent for those portions that can be common to both. For use as a heparin filter, the fiber lumens no need to longer communicate with the outer surface of the device, since oxygenating gas need not be introduced. Present FIG. 3, for instance, shows the heparin filter (11) including cylindrical outer housing (14) and peripheral outer wall (34), as well as base region (36), outer casing (12) and blood outlet port (40). The gas cap of the '334 embodiment is replaced with a simple protective cap (19), while the heat exchanger and bottom cap (20) of the '334 are replaced with a reconfigured bottom header cap (21), having an entrance port (27).

In use, blood to be treated is introduced into the core through the entrance of the bottom cap and through the blood inlet end of the core. From there, the blood flows upwardly into the lumen of the core toward the circumferential rib and window array at the uppermost end of the core. The blood flows through the winds, over the round lip of the lumen and into the plurality of recesses or relieved regions filling the inlet manifold, provided by the space between the innermost region of the fiber bundle and the outside surface of the lumen of the core. From the inlet manifold the blood flows radially away from the core all along the length of the core between the upper and lower potted regions. The blood flows radially through the fiber bundle (70) over the outside of the fibers, and enters the outlet manifold evenly along the length from the top to the bottom thereof. The blood collects in the outlet manifold, particularly in the eccentric collection region adjacent the base of the filter module, and exits the module through the blood outlet. Such an oxygenator would be further modified by providing the microfibers of the bundle with outer surfaces adapted to remove the blood component of interest, e.g., in the form of polyalkyleneimine-coated surfaces, in the manner described herein.

A particularly preferred heparin filer has the ability to remove enough heparin to effectively de-heparinize a fully anticoagulated CPB patient. Typically, mean patient weight is 80KG, and mean heparin concentration at the end of the CPB case is 2.0–2.5 IU/mL of circulating heparin. For a heparin filter to be effective, therefore, it should remove on the order of 20,000 units of heparin within 5–15 minutes. The capacity of heparin removal is related to the surface area of the device and the material interface affinity for heparin. A chemical suitable polymeric would consist of either charged amino acids, or charged material surface. The heparin filter capacity can be increased using a sandwich surface treatment procedure. One method involves Polymer A+Polymer B+Polymer A, where polymer A is a polyethylimmine solution phase polymer coating, and Polymer B is a hydrogel surface such as polyethylene oxide. The capacity of heparin removal can be enhanced by controlling the number of layers in the "sandwich" coating and/or by controlling the polymer concentration of the various "sandwich" layers. One preferred chemistry for optimizing heparin removal capacity consists of Polymer A+Polymer B+Polymer A, where in this case polymer A is PEI as stated above, however Polymer B consists of polyacrylic acid in the MW range of about 400,000 to about 5,000,000, and then the final step is a second solution phase coating of polymer A (PEI). The use of the sandwich layer with polyacrylic acid allows for amplification of surface removal capacity of heparin from either blood or buffer.

A sensor module for use in a system as described herein can employ state of the art detectors (e.g., spectrophotometers), circuitry, flow injection analysis and data management. The system is designed to meet specifications gained from surgeons, anesthesiologists, and perfusionist user surveys. These specifications address a system, and its modules, that provides an optimal combination of such features as the ability to be easily and reproducibly manufactured, durability, portability, reliability and low expense, as compared to the present techniques and devices for providing such functions. In its preferred embodiment, the system is a dual plasma monitoring system that employs spectrophotometric measurements that incorporate flow through cell measurements.

FIG. 1 shows a schematic depiction of the manner in which a heparin sensor module and ACT sensor module can be integrated into a CPB circuit (100). In particular, an 8×selector valve (102) is included to direct the flow of plasma derived from plasma separator (104), via peristaltic pump (106). The selector valve controls the flow and mixing of reagents from reagents reservoir (108), which contains the reagents for determining both heparin and ACT. The reagents reservoir (108) is controlled by selector valve (110) and connected to the 8×selector valve by means of holding coil (112). The 2×selector valve, in turn, can be accessed using one or more syringe pumps (114). Upon mixing and incubation, samples can be transferred from the 8x selector valve to corresponding flow cells (116) and (118) and read by means of spectrophotometer (120), with the results displayed in digital form (122).

Plasma can also be mixed with reagents and substrates required for measuring the aprotinin concentration. During the process where the plasma mixes with reagents required for heparin concentration and aprotinin concentration, microliter quantities of plasma from a plasma separator can be mixed with reagents required for ACT measurements, which can be sent to a second flow cell (where kaolin and diatomaceous earth required for ACT time activation). Flow can be stopped and clotting can be monitored until light scatter occurs indicating that clotting of the plasma has occurred. This ACT time measurement can take however long it takes for the plasma to clot (100–800 seconds), during which time the heparin concentration monitoring and the aprotinin measurements can continue. Since the measurements are made within seconds of mixing the plasma and reagents no quenching step is required.

Optionally, and preferably, the system of this invention includes one or more further features such as a "flow injection analysis system", e.g., by incorporating a compact and portable automated sequential injection analysis (SIA) system. In one embodiment, for instance, such a configuration include an multi-position selector valve, a dual port microsyringe pump, and a two channel auxiliary peristaltic pump for waste and rinse lines. The flow injection system can be controlled by a PC software package.

The flow cell configuration can be optimized, for instance, using a quartz glass cell path to ensure that no air entrapment occurs within the flow cell. The flow cell can be installed in any suitable spectrophotometer, e.g., in a dual channel S2000 Ocean Optics fiber-optic spectrophotometer that employs SMA terminated 200-micron fiber optic cable that allows for visible measurements between 400–500 nm wavelength. A thermocouple controlled flow chamber can be incorporated allowing for temperature controlled clotting time measurements and temperature controlled reaction coils for the chromogenic assays to proceed.

Figure 2:
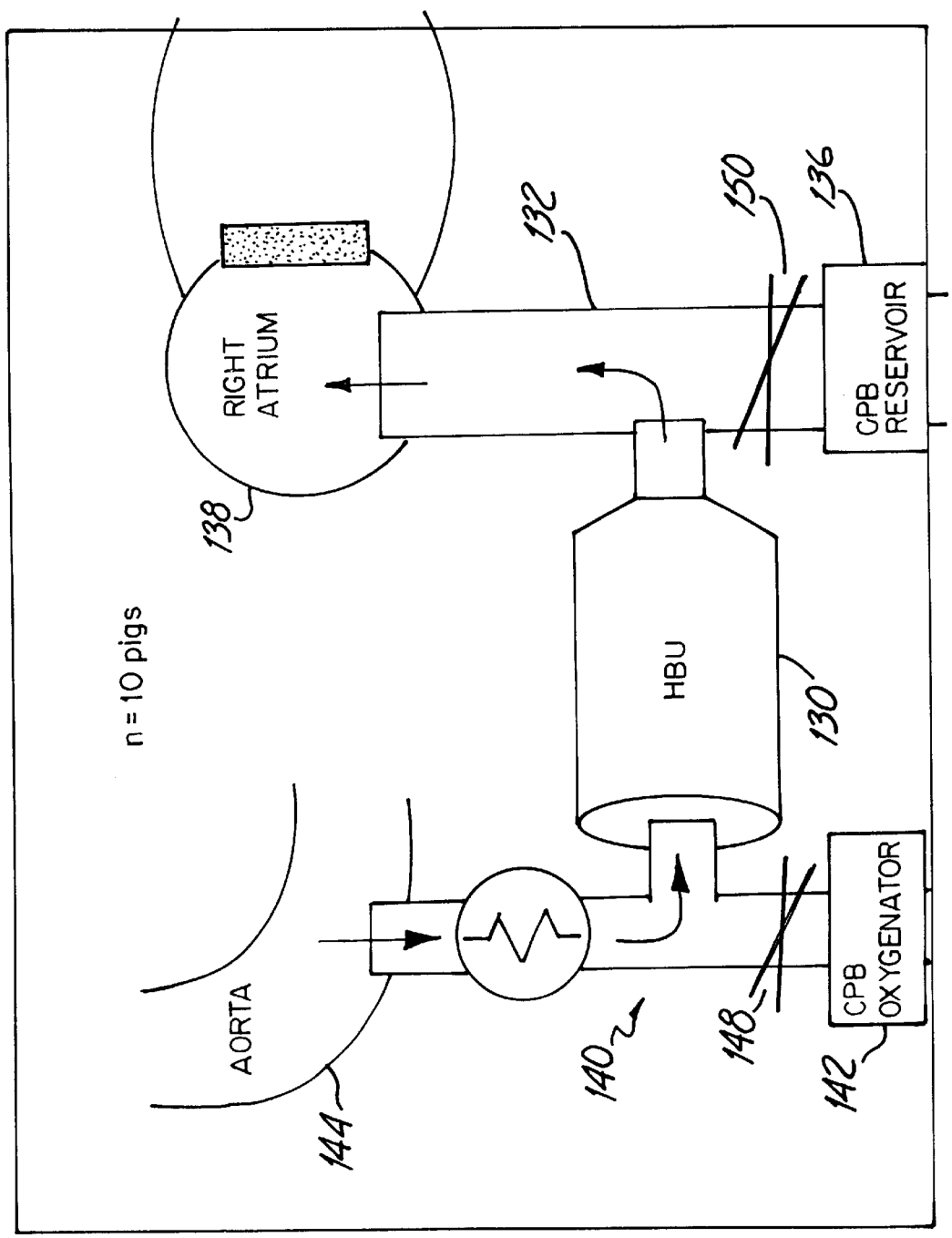
FIG. 2 shows a schematic view of a heparin filter and its placement in a conventional CPB circuit.

A fiber-optic system, as described herein, can be used to perform and read the results of standard methods of heparin concentration and ACT time, using the traditional assays that are currently used in clinical laboratories. The present system provides an added advantage, however, by eliminating the need for manual blood draws, and by the ability to miniaturize the various modules Heparin monitoring can be used to assess both the anticoagulant effects and the level of heparin, and is particularly desirable, since not all patients will achieve a predictable heparin level, nor will a given heparin level reflect an exact state of anticoagulation in any particular patient. A preferred system of this invention therefore further comprises a second module in the form of a heparin filter module, e.g., in the form of an anionic exchange membrane and associated tubing, etc. The anionic exchange membrane can include, for instance, a positively charged (e.g., polylysine, polyethyleneimine) surface. Such a filter can be used to lessen, negate, or more closely control the need for protamine delivery. The filter can be incorporated in any suitable manner in to a conventional CPB system, and is preferably included in the circuit itself. FIG. 2 shows a schematic view of a preferred placement, wherein the heparin filter (130) is positioned within the CPB circuit as a shunt between the flow path (132) between the CPB reservoir (136) and the right atrium (138) and the flow path (140) between the CPB oxygenator (142) and the aorta (144), with both flow paths adapted to being clamped off distally, at points (148) and (150), respectively, beyond the shunt path junction points.

Plasma obtained from a plasma separator unit can be mixed with reagents (e.g., chromogenic substrate and excess Fxa) required for heparin concentration determination, and sent through a flow cell every 15 seconds where it is monitored at 405 nm to provide real time heparin concentrations displayed from a predetermined standard curve. The heparin assay measured by the sensor involves the determination of unfractionated heparins or low molecular weight heparins by the measurement of their anti-Xa activity using the traditional amidoylytic method with the chromogenic substrate according to Teien. This procedure can be carried out with an excess of purified antithrombin III to ensure that existing deficiency of this protein is compensated for. The test principle is based on the in vitro factor Xa inhibition by the antithrombin III-heparin complexes:

ATIII+Heparin →[ATIII-heparin]

[ATIII-heparin]+Xa (excess)→[ATIII-heparin-Xa]+Xa (residual)

Xa (residual)+Chromogenic Substrate→ pNA

The quantity of pNA (paranitroaniline) released at 405 nm is inversely proportional to the amount of heparin present in the plasma. This chromogenic determination of heparin concentration by using Fxa in excess provides an accurate measurement of plasma heparin concentration. This method when incorporated with a fiber optic system using microliter quantities of plasma and reagents provides a quick, accurate and inexpensive means of measuring real time heparin concentration.

The measurement of heparin concentration by the Fxa assay is an accurate and reliable method that is the standard for heparin concentration measurement at most clinical settings. The heparin concentration values obtained by the sensor report concentration of heparin in plasma. The whole blood heparin concentration can easily be determined from the plasma heparin values. This is easily done by adjusting the determined plasma heparin concentration value with the hematocrit values (hematocrit is usually continually monitored using commercially available hematocrit sensors). It has also been reported in the literature that plasma anti-Xa measurements agree with whole blood heparin concentration measurements obtained by automated protamine titration.

The activated clotting time (ACT) is a standard test that can be performed by simply mixing whole blood with a particulate activator (diatomaceous earth) and measuring the time to clot formation. The test has previously been performed manually, as described by Hattersley et al. (JAMA 250:1413 (1983)) or with commercial tubes and automated clot detector. The suggested therapeutic range for the manual method described by Hattersley is 150 to 190 seconds. A typical CPB target ACT range is to maintain clotting time>500 seconds. As automated clot detectors used in operating rooms give somewhat different times, the therapeutic range of heparin management must be established by the individual institution.

During CPB it is essential that coagulation management is performed by analysis of blood clotting performance. Traditionally the ACT assay is used in operating rooms. The ACT an accepted assay, since it can be easily run using whole blood, however the drawback of ACT is poor reproducibility, and the length of the time required for the blood to clot. In addition to the ACT, it is possible to run a number of heparin sensitive clotting time assays using plasma that are more accurate than the traditional ACT. For example, a heparin sensitive Prothrombin (PT), or Thrombin Time (TT) both have the capability of providing useful clot time management information. The Activated Clotting Time (ACT) is a standard test that is performed by simply mixing whole blood with a particulate activator (diatomaceous earth) and measuring the time to clot formation. The test may be performed manually, as described by Hattersley et al. Or with commercial tubes and automated clot detector. The suggested therapeutic range for the manual method described by Hattersley is 15–0190 seconds. A typical CPT target ACT range is to maintain clotting time>500 seconds. As automated clot detectors used in operating rooms give somewhat different times, the therapeutic range of heparin management must be established by the individual institution. In addition to ACT, a heparin sensitive Prothrombin Time (PT) can provide a more accurate, and more reproducible clot time than the ACT. The principle of the PT involves the mixing of plasma with phospholipid (thromboplastin) in the presence of calcium to activate the coagulation system. Baseline unheparinized PT times have a mean of 12.5 seconds, and a heparinized bypass patient is in the range of 45–85 seconds.

A FIA/SIA system to measure aprotinin activity can be designed so that it can easily be tailored to measure the various serine protease factors inhibited by aprotinin. The flow system is designed to measure kallikrein inhibition induced by aprotinin. The principle of that reaction is that FXII in the presence of a contact activator is activated to FXIIa. In the presence of FXIIa prekallikrein is activated to kallikrein. Then, in the presence of kallikrein chromogenic substrate S2302 residual plasma kallikrein activity is measured. The absorbance of p-nitroaniline liberated from the substrate is measured at 405 nm, and inversely proportional to aprotinin concentration.

FXII+contact activator→ FXIIa

FXIIa+prekallikrein→Kallikrein

Kallikrein+S2302 Chromogenic Substrate→ pNA

Results are expressed in KIU as described by Bennett-Guerero. Accuracy of the measurement by the present system can be compared to the values obtained using commercially available kits and reagents purchased commercially, e.g., from Kabi Diagnostica.

FIA/SIA can be tailored to reassure other protease markers affected by aprotinin by utilizing the various commercially available chromogenic substrates. For example there are substrates for plasmin (S2390), Urokinase (S2444), plasminogen, and tissue plasminogen activator (t-PA). Instrumentation settings (reaction times, volumes and temperature) are appropriately set so that accuracy and reproducibility from standard curves are in 95% confidence agreement with commercially available kits which measure aprotinin, heparin and ACT. Testing the assay can be standardized by preparing a series of dilutions of aprotinin in normal plasma. FLA/SIA requires only microliter quantities of reagents and substrates, therefore the assays of aprotinin, heparin and ACT are quick and inexpensive. In addition since FLA/SIA reads samples as the reaction proceeds there is no requirement to quench the reaction.

Flow injection analysis is preferred for use in the present system, in view of its ability to deliver the microliter volumes of plasma and reagents required for various parameters to a detector for analysis. Instrumentation can readily be assembled from simple, inexpensive, off-the-shelf components, and can provide a simple means of automating many manual wet chemical analytical procedures A typical FIA manifold includes, for instance, a pump, injection valve, detector, and tubing manifold. The pump can be used to propel one or more streams through the detector via narrow bore (0.5–0.8 mm ID) tubing. These streams can be reagents, simple buffers, or solvent. The injection valve can be used to periodically introduce a small volume (<100 µl) of sample into the carrier stream. As this sample is carried to the detector, the fluid dynamics of flow through narrow-bore tubing mixes sample and reagent, leading to chemical reaction to form a detectable species. This species is sensed by the detector as a transient peak. The height and area of the peak are proportional to concentration, and are used for quantitation by comparison to samples of known concentration (calibration curve). Although it is possible to carry out the above process in a manual system with detector output to a chart recorder, present systems are computer controlled with appropriate data acquisition and manipulation capabilities.

Detection in the system is generally photometric. Sequential Injection Analysis (SIA) is a new generation of FIA, and was defined by Ruzicka and Marshall in 1991. In SIA, a selection valve and bidirectional pump is used to draw up small volumes of sample and reagents, then propel them through a coil to a detector. Again, the process causes mixing of the sample and reagent segments leading to chemistry which forms a detectable species before reaching the detector. The main benefits of SIA include its simpler hardware as compared to FIA, its efficient use of reagents and minimization of waste, simple and universal manifold, and the ease with which different chemistries can be implemented in one manifold. This benefit is important for in that the system can easily be adapted to measure various assays or methods for heparin, aprotinin, ACT, or other assays.

The use of FIA and/or SIA can include a number of stages, beginning with sampling, where the sample is measured out and injected into the flowing carrier stream (thus, the name Flow Injection Analysis). This step is generally performed with a sample injection valve. The second stage is sample processing. The purpose of this step is to transform the analyte into a species that can be measured by the detector and manipulate its concentration into a range that is compatible with the detector, using one or more of the indicated processes. The third stage is detection where the analyte, or a derivative of it, generates a signal peak which is used for quantitation. The power of FIA as an analytical tool lies in its ability to combine these analytical functions in a wide variety of different ways to create a broad range of different methodologies, and perform these methodologies rapidly and automatically with minute (uL) amounts of sample. FIA can be used to perform chemistry on an analyte to generate a detectable species. Due to the unique processing feature of FIA/SIA, it is possible to run chromogenic assays, such as heparin concentration and aprotinin concentration using low volumes and low cost reagents.

The device most commonly used to measure out the sample and insert it into the FIA carrier stream is a two-position sample. Low-pressure valves, such as the Valco C22 and C24 series, are now available for use in FIA. Preferred valves for use in a system of this invention have an optimal combination of such features as high precision, fast switching, pressure limits of about 100 psi, and the ability to inject sample volumes from a few microliters to several hundred microliters, and in some cases fractions of a microliter.

In a preferred embodiment, plasma is separated from whole blood in a plasma separator unit. A suitable device includes a segment (e.g., about 6 inches in length) of microporous polypropylene fibers encased in ¼" PVC tubing. The fibers are wetted out so that microliter quantities of plasma are continuously removed across the membrane from the whole blood of a patient perfusion. Applicants have discovered that a plasma separator unit of this type can provide plasma for real time analysis with out the requirement of centrifugation.

Using the principle of FIA/SIA as previously described, the plasma is then mixed with reagents required for heparin determination (chromogenic substrate/plasma/FXa required for heparin concentration measurements) and sent through a flow cell every 15 seconds, to be monitored at 405 nm with real time heparin concentrations displayed from a predetermined standard curve. The FIA/SIA device can have a heated reaction coil to allow for the reaction to proceed at 37C. During the process where the plasma mixes with reagents for heparin, microliter quantities of plasma from the plasma separator unit are mixed with reagents required for ACT measurements (Kaolin or diatomaceous earth required for ACT time activation) and sent to a second flow cell. Flow can be stopped and clotting monitored until light scatter occurs indicating the clotting of the plasma has occurred. While heparin and ACT are being measured, a third stream of plasma can be reacted with chromogenic reagents and required substrates for analysis of aprotinin induced Kallikrein inhibition. Once again, the aprotinin reactions can be the standard protease chromogenic reactions measured utilizing FIA/SIA techniques.

A further optional features includes the use of a thermocouple controlled flow chamber, e.g., for use in situations in which temperature controlled clotting time measurements are required. Currently employed whole blood analyzers typically warm the cuvette containing the blood to 37C. for the duration of the clotting time assay. In situations in which temperature control is required for the small volume fiber optic clot meter, or in turn, if measurements are temperature dependent, a suitable temperature regulated flow cell can be incorporated within the system.

An example of a suitable system of this invention includes a dual channel S2000 Ocean Optics fiber-optic spectrophotometer that utilizes SMA terminated 200-micron fiber optic cable that allows for visible measurements between 400–500 nm wavelength. This spectrophotometer can be miniaturized to a palm held device, to provide a device that will fit the miniature size specification required for operating room instrumentation.

EXAMPLES

Example 1

System Evaluation

A fiber optic device is tested for accuracy and reproducibility by comparing a series (n=10) of plasma sample measurements with commercially available kits and reagents. Heparin concentration from the present system are compared to values obtained using the commercially available Fxa kit provided by DiaPharma Coatest Heparin, as well as values obtained by Medtronic's HEPCON system. ACT times are compared to values obtained from the Hemochron and Medtronic HMS. Aprotinin concentration and kallikrein inhibition are compared to values obtained Chromogenix commercially available kits.

Standard curves from known controls are analyzed and closely measured. A system of this invention is calibrated with control levels of plasma, to which the patient's values can be determined. Finally, miniaturized device accurately and reproducibly measures the controls that will serve to calibrate the standard curve.

In the Examples below, in vitro blood loop experimentation is used to compare the accuracy of a system of this invention in following trends of heparin concentration, ACT and KIU. Animal experimentation, as described herein, provides a means to test the system during CPB and using a plasma separator unit, and also allows the opportunity to trace trend accuracy of the present system to existing technologies. Finally, a clinical study as described herein serves to conclusively demonstrate the ability of the system to accurately and inexpensively measure ACT, heparin concentration and aprotinin concentration. The clinical trial portion serves not only as means of evaluating performance, but also provides a means to perform a clinical study to determine the desired effect of heparin concentration and aprotinin concentration.

Example 2

In vitro Blood Loop

In-vitro blood loop testing is performed to analyze the real time coagulation management system with the plasma separator attached. Approximately 1500 mL of freshly drawn porcine whole blood are drawn into a heparinized vacutainer that is preloaded 1500 units of heparin (final concentration 1U/ml heparin). The in-vitro blood loop includes a roller pump, ⅜" PVC tubing and connectors, soft venous bag reservoir, membrane oxygenator and plasma separator. Blood gasses are monitored and conditions are maintained at pH of 7.4, pO2=100 mm Hg, pCO2=40 mm Hg.

During the first set (n=3) of in-vitro experiments heparin concentration is varied while aprotinin concentration is kept constant. For each experiment heparin concentration starts at 1 U/ml and after 30 minutes of continuous measurement reading with the system the heparin dose is increased by 0.5 U/ml final concentration. After each adjustment of heparin concentration measurements is recorded for 30 minutes with the system. Heparin concentrations are compared with values obtained from the commercially available HepCon (Medtronic Hemo Tec, Parker, Colo.) device as well as a microtiter will ELISA based on Fxa. ACT times are compared to values obtained using the commercially available Hemochron 801 (Registered Trademark; International Technidyne, Edison NK)and HepCon HepCon (Medtronic Hemo Tec, Parker, Colo.) systems. For the experiments with varied heparin concentration, aprotinin is set at the beginning of each experiment and left constant for the duration of the experiment. Aprotinin concentrations are either 0, the equivalent of a Half Hammersmith, or the equivalent of a Full Hanmersmith. A total of n=9 in-vitro varied heparin concentration experiments are performed (n=3 for each aprotinin concentration). Results are recorded in the following fashion:

For the second set of in-vitro blood experiments (n=3), heparin concentration are constant at 2.0U/ml heparin concentration and aprotinin concentration is increased in 30-minute intervals. The range of aprotinin is started at zero and increased in increments to the equivalent of a Full Hammersmith concentration. During this set of experiments all of the parameters listed above are monitored. Statistical analysis of all measurements are recorded and comparison between the monitoring system is made with commercially available measurement systems.

Example 3

Porcine Cardiopulmonary Bypass

An experiment is performed in which 6 pigs are placed on cardiopulmonary bypass for 2 hours. An initial heparinization of 300U/kg is administered to the pigs, and a Half-Hammersmith dosage of aprotinin is administered pre-bypass, with no further administration of aprotinin. During the two-hour bypass no adjustment to heparin is. Reading of ACT, Heparin concentration and aprotinin induced KIU are measured continuously using a system of this invention. In addition ACT is measured using the Hemochron and Hep-Con. Heparin concentration is measured using the HepCon and commercially available kit. Aprotinin induced KIU is measured in a microtiter well assay. Statistical analysis of all measurements is recorded and comparison made with commercially available measurement systems.

All animal care is in compliance with the "Principles of Laboratory Animal Care" formulated by the National Society for the Medical Research and the "Guide for the Care and Use of Laboratory Animals" prepared by the National Institutes of Health (NIH Publication No. 86–23, revised 1985). Following review and approval by the Institutional Animal Care and Use Committee, unmedicated and fasting pigs are studied. General anesthesia is induced using intramuscular telazol (4 mg/kg) and xyline (2 mg/kg). An intravenous catheter is placed in an ear vein for administration of medications and intravenous fluids. A cannula is surgically inserted into the carotid artery for mean arterial pressure measurements and blood sampling. A pulmonary artery catheter is surgically placed via an internal jugular vein for hemodynamic monitoring. This is followed by intravenous pancrounim 0.75 mg/kg for nueromuscular blockade. The animal is then intubated via the oral tracheal route and mechanically ventilated using a penlon Anesthesia ventilator AV500. Arterial blood gasses are obtained periodically. Anesthesia is maintained with halothane 1–2% of insipataory volume and a mixture of 70% nitrous oxide and 30% oxygen.

Figure 4:
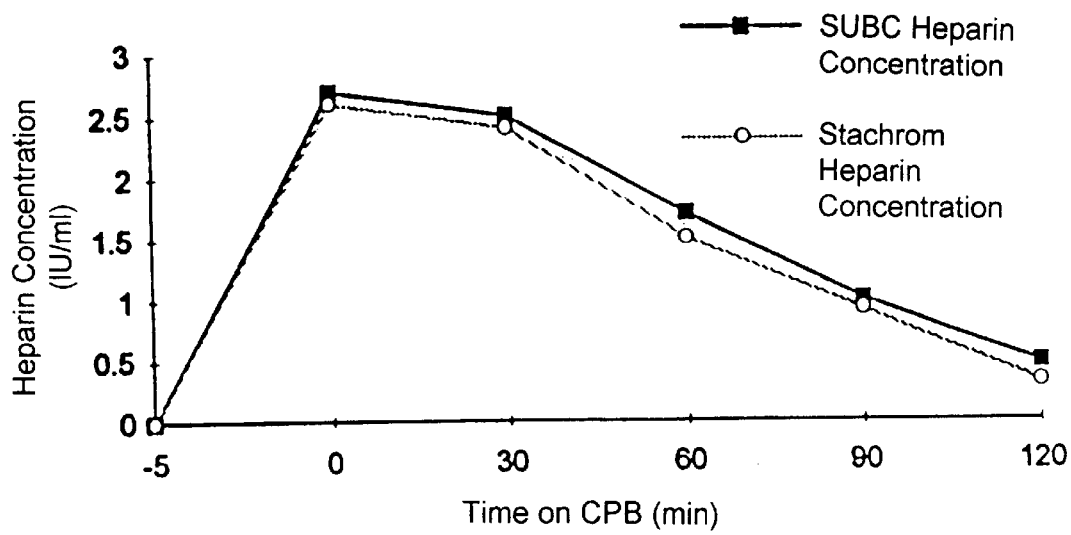
FIG. 4 shows plots comparing heparin and ACT over time, as described in Example 3.
Figure 4:
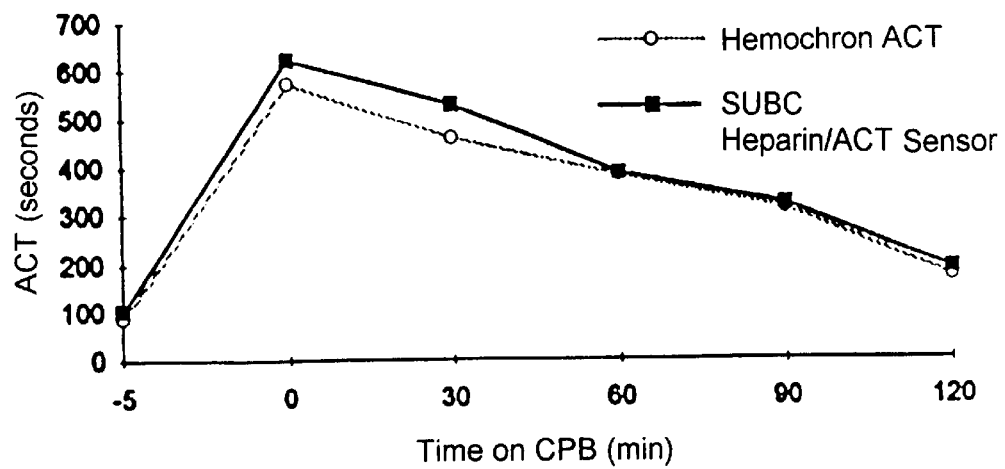

Baseline hematologic parameters of hematocrit (Hct), platelet count, plasma-free hemoglobin, total protein, heparin concentration, activated partial thromboplastin time, ACT, KIU and fibrin split products are obtained. The animal is placed in the right lateral recumbency position. A left side thoracotomy is performed and the pericardium opened. Purse string sutures are placed in the ascending aorta and the right atrial appendage. A 16FR single lumen catheter is placed in the ascending aorta and secured. A 32 FR single lumen catheter is placed in the superior vena cava via artiotomy. The CPB circuit is primed with 1000 ml plasma-lyteA and 500 ml of 6% Hepsan. Cardiopulmonary bypass is then initiated with the use of a hollow fiber membrane oxygenator, a heat exchanger for temperature control, a roller pump and an arterial filter. CPB flow is maintained between 1.5–2.0 L/min and titrateed to maintain a mean arterial pressure of 50–60 mmHG. Oxygen gas flow is initiated at 1.0 liter per minute and the animal remains normothermic. Circuit temperature and arterial blood gases are determined in line using the CDI 400 (Cardiovascular Devices Inc.). This set of animal experimentation provides in vivo results demonstrating the usefulness of the system. Trends of ACT, heparin concentration and KIU over time can be traced with the system and compared with other means of measurements. The performance of the system can be compared to the other values and statistical analysis performed to rank performance characteristics. Representative results of an experiment performed in this manner are shown in FIG. 4, which shows plots demonstrating the ability to monitor both heparin and ACT over time and in the course of CPB.

Example 4

Clinical Evaluation

Clinical evaluation of a system of this invention is performed in the course of a clinical trial. Following Institutional Review Board approval and patient consent, 100 non consecutive adult patients undergoing cardiac surgery requiring CBP are recruited. No alterations in surgical, anesthetic, or postoperative care occur as a result of this study. Patients receive an intravenous fentanyl, midazolam and pancuronium anestheic supplemented with inhaled islflurane. Heparin, 9,000 units/m2 of body surface area is administered intravenously before establishing CPB. Additional 10,000 units of heparin is added to the CPB prime volume of 1.6–1.8 liters.

Aprotinin (Trasylol[r]Bayer Corporation Pharmaceutical Division, West Have, CT is administered as follows to all patients:

$2 \times 10^6$ KIU upon skin incision $0.5 \times 10^6$ KIU/hr on initiation of CPB $2 \times 10^6$ KIU added to the pump prime The ACT is measured 10 minutes (using both HepCon Medtronic Hemo Tec, Parker, CO, and the Hemochron 801 (Registered Trademark; International Technidyne, Edison NK) after heparin administration and every 30 minutes during CPB. Additional heparin is administered if the ACT falls to less than 450 seconds. Intraoperative red blood cell salvage is used for all patients. ACT management is governed using the standard Hemochron 801 (Registered Trademark; International Technidyne, Edison NK) ACT times. Patients are observed for the requirement of alogenic hemostatic blood products (Platelets, frosh frozen plasma, and/or crytprecipate). Patient demographic, and transfusion profiles are summarized. Cumulative chest tube drainage for each observation period for primary, repeat, combined and repeat/combined procedures are analyzed. Mediastinal chest tube drainage, and fresh frozen plasma, and platelet transfusions during the procedure are recorded.

For aprotinin measurements plasma samples are analyzed using the amidolytic substrate assay of commercially available kits. Heparin concentration are measured during the procedure using the Medtronic Hepcon as well as from plasma samples using the amidolytic substrate assay based on Fxa inhibition. The system is used to measure ACT, heparin concentration and KIU, and to monitor these parameters continuously for the duration of CPB.

After completion of the 100 patient study, statistical analysis is performed to compare the accuracy of the measurement of the system to the values obtained using different techniques and instrumentation. In addition the range of aprotinin concentration variation during CPB is recorded. Statistical analysis of KIU range is measured on transfusion requirement and chest tube drainage. The data base from this study allows thorough study of aprotinin concentration and patient outcome in terms of transfusion requirements and chest tube drainage. This is of particular interest since it has been reported that concentrations of approximately 50 KIU/ml decrease fibrinolysis through inhibition of Plasmin, however a higher concentration (approximately 200 KIU) appears to be necessary in order to inhibit kallikrein (REF). The system of this invention provides the opportunity for accurate dosing and recording of aprotinin concentration. The results of this study can also be used to demonstrate what the real implication of aprotinin management can mean in terms of chest tube drainage, transfusion requirements and the monetary cost of intervention to the patient.

What is claimed is:

1. A system for use in combination with an extracorporeal blood flow circuit, the system comprising:
   a) one or more automated sensor modules adapted to monitor, directly or indirectly, the presence of one or more blood parameters, and
   b) one or more regulating modules adapted to affect the presence, concentration and/or activity of one or more blood parameters, wherein the system comprises at least one sensor module that is adapted to incorporate flow injection analysis ("FIA") techniques, and that comprises: i) a blood withdrawal component with in-line access, ii) an analytical component, and iii) a readout component.

2. A system according to claim 1 wherein the monitored blood parameter and the regulated blood parameter are the same.

3. A system according to claim 1 wherein the blood parameter is selected from the group consisting of blood analytes and blood functions.

4. A system according to claim 3 wherein the blood analytes are selected from the group consisting of biomolecules, drugs and metabolites, and the blood functions are selected from the group consisting of clotting time, fibrinolytic activity, and immune response.

5. A system according to claim 4 wherein the blood analytes comprise heparin concentration and aprotinin concentration, and the blood functions comprise clotting time.

6. A system according to claim 1 wherein the sensor module provides semicontinuous and/or continuous sampling of the blood, in order to provide substantially real-time digital output readings of the monitored parameter.

7. A system according to claim 1 wherein the regulating modules comprise a filter adapted to remove inflammation mediators from the blood, the filter providing a support surface selected from the group consisting of a specific binding ligand or hydrophobic surface.

8. A system according to claim 7 wherein the inflammation mediators are selected from the group consisting of anaphylatoxins, chemokines, and proinflammatory cytokines, and the support surface comprises a hydrophobic surface selected from the group consisting of acrylic polymers selected from the group consisting of acrylonitrile polymers, copolymers and polymer blends; polysulfones; polyamides selected from the group consisting of Nylon-6, Nylon-6,6, Nylon-11, Nylon-12, Nylon 6,9, Nylon-12; and acrylic and methacrylic ester polymers.

9. A system according to claim 1 comprising a regulating module adapted to remove heparin from the blood stream by anionic exchange of heparin with an immobilized positively charged species on the surface of a membrane.

10. A system according to claim 1 wherein at least one regulating module comprises a filter for the extracorporeal removal of heparin from the blood stream.

11. A system according to claim 10 wherein the removal of heparin is accomplished by anionic exchange of heparin with an immobilized positively charged species on the surface of a membrane contained within the filter.

12. A system according to claim 11 wherein the species are selected from charged amino acids or a charged material surface.

13. A system according to claim 10 wherein the heparin filter comprises a material interface having affinity for heparin.

14. A system according to claim 13 wherein the material comprises either charged amino acids or a charged material surface.

15. A system according to claim 14 wherein the capacity of the heparin filter material is increased by the use of using a sandwich surface treatment procedure in which layers of a plurality of polymers are provided upon the material.

16. A system according to claim 15 wherein the polymers comprise polyethylimmine (Polymer A) and a hydrogel polymer (Polymer B).

17. A system according to claim 16 wherein the layers comprise a sandwich in the form of Polymer A+Polymer B+Polymer A upon the material surface.

18. A system according to claim 1, wherein at least one regulating module comprises an inflammation filter comprising a hydrophobic surface positioned within a flow chamber having blood inlet and blood outlet ports.

19. A system according to claim 18, wherein the inflammation filter is a complement filter.

20. A system according to claim 1 wherein at least one regulating module comprises a heparin filter in the form of a mass transfer device having a microporous hollow fiber bundle.

21. A system according to claim 20 wherein the mass transfer device comprises a hollow fiber bundle wound on a supporting core for radially outward flow of a first fluid.

22. A system according to claim 21 wherein the heparin filter is adapted to to remove enough heparin to effectively de-heparinize a fully anticoagulated patient.

23. A system according to claim 22 wherein the heparin filter can remove on the order of 20,000 units of heparin within 5–15 minutes.

24. A system according to claim 20 wherein the heparin filter is incorporated within the circuit of a conventional CPB system.

25. A system according to claim 24 wherein the filter is provided as a shunt between between the flow path between a CPB reservoir and the right atrium of the heart, and the flow path between the CPB oxygenator and the aorta.

26. A system according to claim 25 wherein both flow paths are adapted to being clamped off distally at points beyond the shunt path junction points.

27. A system according to claim 1 further comprising a system for performing automated sequential injection analysis (SIA) of a plurality of blood parameters or samples.

28. A system according to claim 1 wherein the flow injection analysis further comprises the use of a flow cell and spectrophotometer.

29. A system according to claim 1 wherein the monitoring of blood parameters comprises the use of fiber-optic measurements.

30. A method for monitoring and regulating blood parameters in the course of extracorporeal blood flow, the method comprising:
 a) providing an extracoporeal blood flow circuit comprising, in the order of blood flow, a reservoir, a pump, and oxygenator, a filter, together with associated tubing, connectors and controls,
 b) providing a system comprising
  i) one or more automated sensor modules adapted to monitor, directly or indirectly, the presence of one or more blood parameters, and
  ii) one or more regulating modules adapted to affect the presence, concentration and/or activity of one or more blood parameters.
 c) employing the sensor module(s) to monitor one or more blood parameters, and
 d) employing the filter module(s) to affect the presence, concentration and/or activity of one or more blood components, wherein the system comprises at least one sensor module that is adapted to incorporate flow injection analysis ("FIA") techniques, and that comprises: i) a blood withdrawal component with in-line access, ii) an analytical component, and iii) a readout component.

31. A method according to claim 30 wherein the monitored blood parameter and the regulated blood parameter are the same.

32. A method according to claim 30 wherein the blood parameter is selected from the group consisting of blood analytes and blood functions.

33. A method according to claim 32 wherein the blood analytes are selected from the group consisting of biomolecules, drugs and metabolites, and the blood functions are selected from the group consisting of clotting time, fibrinolytic activity, and immune response.

34. A method according to claim 33 wherein the blood analytes comprise heparin concentration and aprotinin concentration, and the blood functions comprise clotting time.

35. A method according to claim 30 wherein the sensor module provides semicontinuous and/or continuous sampling of the blood, in order to provide substantially real-time digital output readings of the monitored parameter.

36. A method according to claim 30 wherein the regulating modules comprise a filter adapted to remove inflammation mediators from the blood, the filter providing a support surface selected from the group consisting of a specific binding ligand or hydrophobic surface.

37. A method according to claim 36 wherein the inflammation mediators are selected from the group consisting of anaphylatoxins, chemokines, and proinflammatory cytokines, and the support surface comprises a hydrophobic surface selected from the group consisting of acrylic polymers selected from the group consisting of acrylonitrile polymers, copolymers and polymer blends; polysulfones; polyamides selected from the group consisting of Nylon-6, Nylon-6,6, Nylon-11, Nylon-12, Nylon 6,9, Nylon-12; and acrylic and methacrylic ester polymers.

38. A method according to claim 30 wherein at least one regulating module comprises a filter for the extracorporeal removal of heparin from the blood stream.

39. A method according to claim 38 wherein the removal of heparin is accomplished by anionic exchange of heparin with an immobilized positively charged species on the surface of a membrane contained within the filter.

40. A method according to claim 39 wherein the species are selected from charged amino acids or a charged material surface.

41. A method according to claim 38 wherein the heparin filter comprises a material interface having affinity for heparin.

42. A method according to claim 41 wherein the material comprises either charged amino acids or a charged material surface.

43. A method according to claim 42 wherein the capacity of the heparin filter material is increased by the use of using a sandwich surface treatment procedure in which layers of a plurality of polymers are provided upon the material.

44. A method according to claim 43 wherein the polymers comprise polyethylimmine (Polymer A) and a hydrogel polymer (Polymer B).

45. A method according to claim 44 wherein the layers comprise a sandwich in the form of Polymer A+Polymer B+Polymer A upon the material surface.

46. A method according to claim 30, wherein at least one regulating module comprises an inflammation filter comprising a hydrophobic surface positioned within a flow chamber having blood inlet and blood outlet ports.

47. A method according to claim 46, wherein the inflammation filter is a complement filter.

48. A method according to claim 30 wherein at least one regulating module comprises a heparin filter in the form of a mass transfer device having a microporous hollow fiber bundle.

49. A method according to claim 48 wherein the mass transfer device comprises a hollow fiber bundle wound on a supporting core for radially outward flow of a first fluid.

50. A method according to claim 49 wherein the heparin filter is adapted to to remove enough heparin to effectively de-heparinize a fully anticoagulated patient.

51. A method according to claim 50 wherein the heparin filter can remove on the order of 20,000 units of heparin within 5–15 minutes.

52. A method according to claim 30 further comprising a system for performing automated sequential injection analysis (SIA) of a plurality of blood parameters or samples.

53. A method according to claim 30 wherein the flow injection analysis further comprises the use of a flow cell and spectrophotometer.

54. A method according to claim 30 wherein the monitoring of blood parameters comprises the use of fiber-optic measurements.

55. A method according to claim 46 wherein the heparin filter is incorporated within the circuit of a conventional CPB system.

56. A method according to claim 55 wherein the filter is provided as a shunt between between the flow path between a CPB reservoir and the right atrium of the heart, and the flow path between the CPB oxygenator and the aorta.

57. A method according to claim 56 wherein both flow paths are adapted to being clamped off distally at points beyond the shunt path junction points.

58. A method according to claim 11 comprising a regulating module adapted to remove heparin from the blood stream by anionic exchange of heparin with an immobilized positively charged species on the surface of a membrane.

* * * * *

UNITED STATES PATENT AND TRADEMARK OFFICE
CERTIFICATE OF CORRECTION

| | |
|---|---|
| PATENT NO. | : 6,733,471 B1 |
| APPLICATION NO. | : 09/662044 |
| DATED | : May 11, 2004 |
| INVENTOR(S) | : Ericson et al. |

It is certified that error appears in the above-identified patent and that said Letters Patent is hereby corrected as shown below:

Column 21, line 17, that portion of the claim reading "adapted to to remove" should read --adapted to remove--.

Column 21, line 26, that portion of the claim reading "shunt between between the" should read --shunt between the--.

Column 21, line 48, that portion of the claim reading "system comprising" should read --system comprising:--.

Column 21, line 54, that portion of the claim reading "blood parameters." should read --blood parameters,--.

Column 23, line 5, that portion of the claim reading "adapted to to remove" should read --adapted to remove--.

Column 24, line 5, that portion of the claim reading "shunt between between the" should read --shunt between the--.

Column 24, line 12, that portion of the claim reading "to claim 11" should read --to claim 30--.

Signed and Sealed this

Seventeenth Day of April, 2007

JON W. DUDAS
*Director of the United States Patent and Trademark Office*